United States Patent [19]

Almond et al.

[11] Patent Number: 5,286,640
[45] Date of Patent: Feb. 15, 1994

[54] ATTENUATED POLIOVIRUSES

[76] Inventors: Jeffrey W. Almond, Department of Microbiology, University of Reading, London Road, Reading RG1 5AQ; Michael A. Skinner, Medical Research Council Laboratory of Molecular Biology, Hills Road, Cambridge CB2 2QH, both of United Kingdom; Vincent Racaniello, Dept. of Microbiology College of Physicians & Surgeons of Columbia University, 701 W. 168th St., New York, N.Y. 10032; Philip D. Minor, National Institute of Biological Standards & Control, Blanche Lane, South Mimms Potters Bar Herts EN6 3QG, United Kingdom

[21] Appl. No.: 62,046
[22] PCT Filed: Jan. 5, 1989
[86] PCT No.: PCT/GB89/00004
§ 371 Date: Jul. 19, 1990
§ 102(e) Date: Jul. 19, 1990
[87] PCT Pub. No.: WO89/06277
PCT Pub. Date: Jul. 13, 1989

Related U.S. Application Data

[63] Continuation of Ser. No. 543,759, Jul. 19, 1990, abandoned.

[30] Foreign Application Priority Data

Jan. 5, 1988 [GB] United Kingdom ............... 8800100

[51] Int. Cl.$^5$ .................. C12N 7/04; C12N 15/09; C12N 7/01; A61K 39/13
[52] U.S. Cl. .................. 435/236; 435/172.3; 424/93 A
[58] Field of Search ............. 435/236, 172.3; 424/93 A

[56] References Cited

FOREIGN PATENT DOCUMENTS 0323900 7/1989 European Pat. Off. ...... C12N 7/00
0325768 8/1989 European Pat. Off. ...... C12N 15/00
0383433 8/1990 European Pat. Off. ...... C12N 15/41
60-207582 3/1986 Japan .......................... C12N 15/43

OTHER PUBLICATIONS

Kuge et al. (May, 1987), J. Virol. vol. 61(5), pp. 1478–1487.
Almond et al J. Virol. Meth, vol. 17 (1–2) (1987).
La Monica et al J. Virol. vol. 61 (9) (1987) pp. 2917–2920.
Gillis Dewalt et al J. Virol. vol. 61 (7) (1987) pp. 2162–2170.
Toyoda et al. (1984), J. Mol. Biol. 124: 263–270.
Pilipenko et al. (1989), Virology 168: 201–209.
Pelletier et al. (1988), J. Virol. 62 (12): 4486–4492.
van der Werf et al. (1986), Proc. Natl. Acad. Sci USA 83: 2330–2334.
Blinov et al. (1988), Biochem. Genetics 108: 144 367w.
Almond et al. (1988), Chem. Abstracts 109: 228 104s.
P. D. Minor et al. "The effect of sequences in the 5' . . . ." J. Gen. Virol. (1988) 69, pp. 1091–1096.
A. Z. Zelent et al. "Replicative Intermediate of . . . " J. Virol., (Sep. 1987), vol. 61, pp. 2921–2923.
Ruibao Ren et al. "Identificaation of two determinants . . . " Jour of Virology (Mar. 1991), vol. 65 No. 3, pp. 1377–1382.
A. J. Macadam et al. "The 5' Noncoding region of the typw 2 . . . " Virology (1991), 181, pp. 451–458.
Stanway et al, Proc. Natl. Acad. Sci. U.S.A., vol. 81 pp. 1539–1543, Mar. 1984.
Nomoto et al, Proc. Natl. Acad. Sci. U.S.A., vol. 79 pp. 5793–5797, Oct. 1982.
Evans et al, Nature vol. 314, Apr. 11, 1985 548–550.
Rivera et al, Virology 165, 42–50 (1988).
La Monica et al, Journal of Virology, vol. 57 No. 2, Feb. 1986, pp. 515–525.
Svitkin et al. Virology 166, 394–404 (1988).
Skinner et al, J. Mol. Biol. (1989) 207, 379–392.
Stanway et al, J. Virology, Mar. 1986, pp. 1187–1190.

Primary Examiner—Richard A. Schwartz
Assistant Examiner—Philip W. Carter
Attorney, Agent, or Firm—Nixon & Vanderhye

[57] ABSTRACT

An attenuated enterovirus or rhinovirus, suitable for use as a vaccine, has an attenuating mutation at least at a position which is, or corresponds with, position 479 and/or 482 of poliovirus type 3 Leon strain.

10 Claims, No Drawings

ATTENUATED POLIOVIRUSES

This is a continuation of application Ser. No. 07/543,759, filed Jul. 19, 1990, now abandoned.

This invention relates to construction of vaccines against rhinoviruses and enteroviruses, particularly polioviruses, by the introduction of defined mutations into their genomes. These mutations attenuate the virulence of wild type viruses and can further attenuate existing live attenuated vaccine virus strains, thereby making them less likely to revert to virulence.

At the present time, the only vaccines routinely used against enterovirus and rhinovirus infections are those against poliomyelitis. Of these the live attenuated vaccines developed by Sabin in the 1950's have found greatest use throughout the world. Vaccine strains derived from each of the three poliovirus stereotype (P1, P2 and P3) were prepared by passage of wild type viruses in cell cultures and whole animals until attenuated strains were obtained. These attenuated viruses are substantially less able to cause poliomyelitis in humans than the original wild type strains. They are administered orally and replicate in the gut to induce a protective immune response.

Although these vaccines are generally regarded as safe, their use is associated with a low level of paralysis in vaccinees. This is most often associated with type 2 and type 3 serotypes and rarely, if ever, with type 1. There is therefore a requirement for improved type 2 and type 3 vaccines which would be comparable in safety to the excellent type 1 strain. There is also a requirement for vaccines against other enteroviruses, e.g. echo, coxsackie and hepatitis A, and against rhinoviruses.

The Sabin vaccine strains were developed by essentially empirical procedures. The genetic basis of their attenuation is not properly understood. Over the past few years, however, scientists have employed a number of molecular biological techniques in an attempt to elucidate the mechanism by which the neurovirulence of these vaccine strains is reduced. Most of the work has concentrated on serotypes 1 and 3. For both of these the complete nucleotide sequences of the vaccine strains have been compared with those of their neurovirulent progenitors.

In the case of poliovirus type 1, the vaccine strain differs from its progenitor at 47 positions in the 7441 base genome (Nomoto et al, 1982, *Proc Natl Acad Sci U.S.A.* 79: 5793–5797). All of these are simple point mutations and 21 of them give rise to amino acid changes in virus coded proteins. Although several mutations are thought to contribute to the attenuation phenotype of the vaccine strain, direct evidence has been presented that the mutation of A to G at position 480 in the 5' non-coding region of the genome has a marked attenuating effect on the virus (Nomoto et al, 1987, UCLA *Symp Mol Cell Biol*, New Series, Vol 54 (Eds M A Brinton and R R Rueckert), 437–452, New York: Alan R Liss Inc).

Analogous studies on poliovirus type 3 reveal just 10 nucleotide sequence differences in the 7432 base genome between the vaccine and its progenitor strain (Stanway et al, 1984, *Proc Natl Acad Sci U.S.A.* 81: 1539–1543). Just three of these give rise to amino acid substitutions in virus encoded proteins. The construction of defined recombinants between the vaccine and its progenitor strain has allowed the identification of the mutations which contribute to the attenuation phenotype. One of these is at position 2034 and causes a serine to phenylalanine change in virus protein VP3.

The other mutation of interest is C to U at position 472 in the 5' non-coding region of the genome. This latter mutation has been observed to revert to the wild type C rapidly upon replication of the virus in the human gut (Evans et al, 1985, *Nature* 324: 548–550). This reversion is associated with an increase in neurovirulence. C at position 472 has also been shown to be essential for growth of a mouse/human polio recombinant virus in the mouse brain (La Monica et al, 1986, *J Virol* 57: 515–525). Recently, we have observed that at 481 in poliovirus type 2 A changes to G in an analogous fashion upon replication of the type 2 vaccine in the gut of vaccinees.

We have investigated mutations of the wild-type poliovirus type 3 Leon strain at several sites in the 5' non-coding region approximately spanning nucleotides 450 to 510. We found that poliovirus with a mutation at position 479 or 482 is attenuated but with a mutation at position 480 is non-attenuating. Multiple mutations were frequently lethal. However, Poliovirus with a double mutation at positions 472 and 482 was more highly attenuated than poliovirus with a single mutation at either position.

The findings can be extrapolated to all polioviruses. indeed, they may be extrapolated to other enteroviruses and rhinoviruses. Mutations at sites of other-enteroviruses and rhinoviruses corresponding to position 479 and/or 482 and, optionally, position 472 of poliovirus type 3 Leon strain can lead to attenuation. There is a relatively high degree of homology between the genome RNA of all enteroviruses and rhinoviruses. The positions of another strain of enterovirus or rhinovirus corresponding to positions 472, 479 and 482 of poliovirus type 3 Leon strain (based on the numbering used in the Stanway et al paper already referred to) can be determined by lining up the sequences of the genomic RNA of the strains.

Accordingly the invention relates to attenuated enteroviruses and rhinoviruses having an attenuating mutation at least at a position which is, or corresponds with, position 479.and/or 482, and optionally also position 472, of the genome of poliovirus type 3 Leon strain.

The present invention is particularly applicable to polioviruses. We have found in particular that the mutation A to C at position 479 of the genome of poliovirus type 3 Leon strain causes attenuation, as does nutation G to A at position 482. Either or both may be combined with the mutation C to U at position 472. We have further found that poliovirus type 3 with mutations at both positions 472 and 482 is more highly attenuated than viruses with mutations at either one of the positions.

An attenuated poliovirus may be a type 1, type 2 or type 3 poliovirus. Types 2 and 3 are preferred. For types I and 2, positions 476, 479 and 469 correspond to positions 479, 482 and 472 respectively of poliovirus type 3. An attenuated type 1 or type 2 poliovirus therefore includes an attenuating mutation at position 476 and/or 479 and, optionally, also at position 469. These mutations may be as above for type 3.

An attenuated virus according to the invention is prepared by a process comprising:

(i) introducing the or each desired mutation by site-directed mutagenesis into a sub-cloned region, which includes the or each position it is wished to mutate, of a cDNA copy of the genome of an enterovirus or rhinovirus;

(ii) reintroducing the thus modified region into the complete cDNA from which the region was derived; and (iii) obtaining live virus from the cDNA thus obtained.

A mutation can be introduced into a strain of an enterovirus or rhinovirus, for example wild-type virus, by site-directed mutagenesis of a cDNA copy of its genomic RNA. This may be achieved beginning with subcloning the appropriate region from an infectious DNA copy of the genome of any of the virus strain, for example a vaccine strain or its progenitor, into the single strand DNA of a bacteriophage such as M13. The virus strain may be a neurovirulent strain but is preferably a vaccine strain. For poliovirus it may be a Sabin, type 3 Leon or type 1 Mahoney strain. The or each desired nutation is then introduced into this sub-cloned cDNA using the technique of oligonucleotide directed mutagenesis.

After the introduction of mutations, the modified sub-cloned cDNAs are reintroduced into the complete cDNA from which they were derived and, for virulence testing in mice, into a cDNA derived from a murine poliovirus derivative known to cause a poliomyelitis type disease in mice (La Monica et al). Live virus is recovered from the mutated full length cDNA by production of a positive sense RNA typically using a T7 promoter to direct transcription in vitro (Van der Werf et al, 1986, *Proc Natl Acad Sci*, U.S.A. 83:2330–2334). The recovered RNA may be applied to tissue cultures using standard techniques (Koch, 1973, *Curr Top Microbiol Immunol* 61:89–138). After 4–6 days incubation virus can be recovered from the supernatant of the tissue culture. The level of neurovirulence of the modified virus may then be compared with that of the unmodified virus using a standard LD50 test in mice (La Monica et al) or the WHO approved vaccine safety test in monkeys (*WHO Tech Rep Ser* 687: 107–175, 1983).

The attenuated viruses can be used as vaccines. They may therefore be formulated as pharmaceutical compositions further comprising a pharmaceutically acceptable carrier or diluent. Any carrier or diluent conventionally used in vaccine preparations may be employed. For example, the presently used live attenuated poliovirus strains are stabilised in a solution of 1 molar $MgCl_2$ ana administered as a mixture of the three serotypes.

The attenuated viruses can therefore be used to prevent an infection attributable to an enterovirus or rhinovirus in a human patient. For this purpose, they may be administered orally, as a nasal spray, or parenterally, for example by subcutaneous or intramuscular injection. A dose corresponding to the amount administered for a conventional live virus vaccine, such as up to $10^6$ $TCID_{50}$ for a Sabin vaccine strain in the case of poliovirus, may be administered.

The following Example illustrates the invention.

EXAMPLE

A HindIII-SstI fragment from a cDNA clone of P3/Leon/37, which includes the first 751 base pairs of the genome, was sub-cloned into the phage vector M13mp9. P3/Leon/37 is the neurovirulent progenitor of the type 3 vaccine strain. Mutations were then introduced into this sub-cloned cDNA fragment using the technique of oligonucleotide directed mutagenesis. The chemically synthesised DNA oligonucleotides used are shown in Table 1 below:

TABLE 1

| Oligonucleotide No | Sequence (5'-3') |
|---|---|
| 1 | GCC-TGC-TCC-ATG-GTT-ATA-TTT-AGC-CGC-ATT |
| 2 | GCC-TGC-TCC-ATG-GTT-ATG-TTT-AGC-CGC-ATT |
| 3 | GCA-GCT-GCC-TGC-CTC-ATT-TTT-AGA-GTT-AGC-CGC-ATT-CAG-C |
| 7 | GCT-GCC-TGC-TTC-ATG-GTT |
| 8 | GCT-GCC-TGC-TTC-ATG-CTT-AGA-ATT-AGC-CGC-A |
| 9 | GCT-GCC-TGC-TGC-ATG-GTT-AGC-ATT-AGC-C |
| 11 | GCT-GCC-TGC-TCC-CAT-GGT-TAG-GAA-TTA-GCC |
| 12 | GCT-GCC-TGC-TAT-TAG-CCG |
| 13 | CCT-GCT-CCA-GGG-TTA-GG |
| 14 | CCT-GCT-CCG-TGG-TTA-GG |

The sequence from base 470 to 484 of the genomic RNA of poliovirus type 3 Leon strain and of mutants derived from this strain is shown in Table 2 below. Mutations are shown by lower case letters. The viability of the strains is also shown, "+" meaning viable and "−" meaning not. Of the viable strains, the parental Leon strain and mutant 14 are virulent. Mutants 7, 8 and 13 are attenuated.

TABLE 2

| Mutant | Sequence (470–484) | Viability |
|---|---|---|
| (Leon | AUCCUAACCAUGGAG | +) |
| 1 | AauaUAACCAUGGAG | − |
| 2 | AaCaUAACCAUGGAG | − |
| 3 | AcuCUAAaaAUGagG | − |
| 7 | AUCCUAACCAUGaAG | + |
| 8 | AUuCUAACCAUGaAG | + |
| 9 | AUgCUAACCAUGcAG | − |
| 11 | AUuCcUAACCAUgGGAG | − |
| 12 | AUAG | − |
| 13 | AUCCUAACCcUGGAG | + |
| 14 | AUCCUAACCAcGGAG | + |

Mutant 7 (Table 2) was constructed by hybridising oligonucleotide 7 in Table 1 to the single stranded cloned DNA fragment in M13 phage. This oligonucleotide is complementary to the region 475-492 except at the position to be mutated, where the base complementary to the desired mutation is incorporated. In other words, oligonucleotide 7 contains U instead of C at the position complementary to base 482. The hybridised M13 and oligonucleotide DNA were incubated in a reaction mixture containing DNA precursors and the enzymes DNA polymerase and DNA ligase. After incubation for one hour at 37° C., closed circular DNA was isolated from this mixture by agarose gel electrophosesis. This DNA was then used to transform *E coli* muts or mutt (deficient in DNA mismatch repair) which were then plated out on a lawn of *E coli* JM101.

M13 plaques which arose on this lawn of *E coli* were picked and propagated and single stranded M13 phage DNA isolated. The DNAs were then sequenced using the method of Sanger and those with the desired mutation were identified. From these, batches of replicative form double stranded DNA were prepared and the HindIII-SstI fragment containing 751 base pairs of infectious poliovirus cDNA, which incorporates the mutation, was recovered.

The mutated cDNA fragment was then reintroduced into a derivative of pVN23 which had been modified to include a T7 promoter. Live virus was recovered from the mutated full length cDNA by the production of a positive sense RNA transcript from the T7 promoter in vitro (Van der Werf et al) which was applied to Hela cells in tissue culture using standard techniques (Koch). After 4 to 6 days incubation a cytopathic effect was observed and virus could be recovered from the supernatant.

Recovered virus was plaque purified and propagated in Hela cells. This virus pool was used for the preparation of RNA on which the sequence of the virus mutant was verified using primer extension nucleotide sequencing. A portion of the pool was also used to assay neurovirulence using techniques described previously. The LD50 for mutant 7 was $7.5 \times 10^6$ pfu (compared to $>2 \times 10^7$ pfu for the vaccine derivative and $<6 \times 10^2$ pfu for the neurovirulent progenitor derivative), indicating that this mutation has a definite attenuating effect on the virus.

This procedure was repeated for oligonucleotides 1 to 3, 9 and 11 to 14. Testing of virus recovered from mutant cDNA 13 (i.e. A to C at 479) revealed that this mutation also had a definite attenuating effect on virulence (LD50=$9.1 \times 10^6$). Conversely, testing of virus recovered from mutant cDNA 14 revealed that this mutation (i.e. U to C at 480) had little or no effect on neurovirulence (LD50=$<7 \times 10^4$). Attempts to recover virus from mutant cDNAs 1, 2, 3, 9, 11 and 12 resulted in failure, indicating that they contain mutation(s) lethal for the virus.

The procedure was also repeated for oligonucleotide 8. Mutant cDNA 8 was constructed which contained both the mutations which are separately attenuating in the vaccine strain (i.e. C to U at 472) and in mutant 7 (i.e. G to A at 482). Virus recovered from this double mutant cDNA was tested for neurovirulence and found to have an LD50 of $>4.8 \times 10^7$ pfu. This double mutant is therefore more attenuated than either the vaccine strain or mutant 7.

We claim:

1. An attenuated poliovirus having an attenuating nutation at least at a position which is, or corresponds with, position 479 and/or 482 of the genome of poliovirus type 3 Leon strain.

2. An attenuated virus according to claim 1, which is a type 1 poliovirus.

3. An attenuated virus according to claim 1, which is a type 2 poliovirus.

4. An attenuated virus according to claim 1, which is a type 3 poliovirus.

5. An attenuated virus according to claim 1, in which the base at position 479 or at a said corresponding position is cytosine.

6. An attenuated virus according to claim 1, in which the base at position 482 or at a said corresponding position is adenine.

7. An attenuated virus according to claim 1, which also has an attenuating nutation at a position which is, or which corresponds with, position 472 of poliovirus type 3 Leon strain.

8. An attenuated virus according to claim 7, which is a poliovirus which has the base U at position 472 or at a said corresponding position.

9. A pharmaceutical composition comprising a pharmaceutically acceptable carrier or diluent and an attenuated virus as claimed claim 1.

10. A method of vaccinating a patient against a poliovirus, which method comprises administering thereto an effective amount of an attenuated virus as claimed in claim 1.

* * * * *